United States Patent
Delaney, Jr. et al.

(10) Patent No.: US 12,404,369 B2
(45) Date of Patent: *Sep. 2, 2025

(54) MULTI-ARMED POLYOXAZOLINES AND COMPOSITIONS, SYSTEMS AND METHODS PERTAINING TO THE SAME

(71) Applicant: Boston Scientific Scimed Inc., Maple Grove, MN (US)

(72) Inventors: Joseph T. Delaney, Jr., Minneapolis, MN (US); Paul V. Grosso, Maple Grove, MN (US); John Kummailil, Sherborn, MA (US); Tatyana Dyndikova, Minneapolis, MN (US); Carey Rehder, Inver Grove Heights, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/475,397

(22) Filed: Sep. 27, 2023

(65) Prior Publication Data

US 2024/0026081 A1 Jan. 25, 2024

Related U.S. Application Data

(63) Continuation of application No. 16/999,787, filed on Aug. 21, 2020, now Pat. No. 11,807,720.

(Continued)

(51) Int. Cl.
    C08G 73/02 (2006.01)
    C08J 3/24 (2006.01)
    A61L 27/52 (2006.01)

(52) U.S. Cl.
    CPC ............ *C08G 73/0233* (2013.01); *C08J 3/24* (2013.01); *A61L 27/52* (2013.01)

(58) Field of Classification Search
    None
    See application file for complete search history.

(56) References Cited

U.S. PATENT DOCUMENTS

| 5,804,664 A | 9/1998 | Kennedy et al. |
| 5,844,056 A | 12/1998 | Kennedy et al. |

(Continued)

FOREIGN PATENT DOCUMENTS

| EP | 3446721 A1 | 2/2019 |
| WO | 2005028539 A2 | 3/2005 |
| WO | 2017157188 A1 | 9/2017 |

OTHER PUBLICATIONS

Kirila et al., "Features of Solution Behavior of Polymer Stars with Arms of Poly-2-alkyl-2-oxazolines Copolymers Grafted to the Upper Rim of Calix[8]arene," Polymers 13, No. 15: 2507. https://doi.org/10.3390/polym 13152507 (Year :2021).

(Continued)

*Primary Examiner* — Megan McCulley
(74) *Attorney, Agent, or Firm* — Seager, Tufte & Wickhem LLP

(57) ABSTRACT

In some aspects, the present disclosure pertains to a multi-arm polymer comprising a core and a plurality of polyoxazoline segments (or arms) having a first end that is covalently attached to the core and a second end comprising a moiety that comprises a reactive group. In some aspects, systems are provided that comprise a first composition comprising such a multi-arm polymer and a second composition comprising a multifunctional compound that comprises functional groups that are reactive with the reactive groups of the multi-arm polymer. In some aspects, systems are provided that comprise crosslinked reaction products of such a multi-arm polymer and such a multifunctional compound.

18 Claims, 2 Drawing Sheets

Related U.S. Application Data

(60) Provisional application No. 62/898,791, filed on Sep. 11, 2019.

(56) References Cited

U.S. PATENT DOCUMENTS

| | | |
|---|---|---|
| 6,818,018 B1 | 11/2004 | Sawhney |
| 8,383,161 B2 | 2/2013 | Campbell et al. |
| 2003/0228974 A1 | 12/2003 | Katz et al. |
| 2005/0112088 A1 | 5/2005 | Zhao et al. |
| 2018/0264176 A1 | 9/2018 | Broguiere et al. |
| 2019/0038454 A1 | 2/2019 | Eisenfrats et al. |

OTHER PUBLICATIONS

Hoogenboom et al., "Synthesis and crystal Structures of multifunctional tosylates as basis for star-shaped poly (2-ethyl-2-oxazolines)" Beilstein Journal of Organic Chemistry, vol. 6, pp. 773-783, 2010.

Ten'Kotsev et al., "Thermoresponsive star-shaped poly(2-isopropyl-2-oxazolines) based on octa-tert-butylcalix[8] arene," Polymer Science, Series B, vol. 54, No. 3-4, Apr. 1, 2012.

Dworak et al., "Themosensitive star polymers synthesis and Properties," Polimery-W, vol. 57, No. 6, pp. 441-448, 2012.

England et al., "Tumour regression and improved controlled release of SN-38 from novel polyoxasoline-modified dendrimers," Journal of controlled Release, vol. 247, pp. 73-85, Feb. 1, 2017.

International Patent Search Report and Written Opinion for the International Patent Application No. PCT/US2020/047428, 16 pages, dated Oct. 30, 2021.

"Augmenix Announces positive Three-year SpaceOAR Clinical Trial Results," Imaging Technology News, Oct. 27, 2016.

"Augmenix Receives FDA Clearance to Market its TraceIT™ Tissue Marker," BusinessWire Jan. 28, 2013.

Zhang et al., "Anti-PEG antibodies in the clinic: Current issues and beyond PEGylation," Journal of Controlled Release vol. 244, (Part B), pp. 184-193, 2016.

Salgarella et al., "Investigation of drug release modulation from poly(2-oxazoline) micelles through ultrasound," Scientific Reports, vol. 8, No. 1, p. 9893, 2018.

MULTI-ARMED POLYOXAZOLINES AND COMPOSITIONS, SYSTEMS AND METHODS PERTAINING TO THE SAME

CROSS-REFERENCE TO RELATED APPLICATION

This application is a continuation of U.S. application Ser. No. 16/999,787, filed Aug. 21, 2020, which claims the benefit of U.S. Provisional Application No. 62/892,791, entitled "MULTI-ARMED POLYOXAZOLINES AND COMPOSITIONS, SYSTEMS AND METHODS PERTAINING TO THE SAME" and filed Aug. 28, 2019, the entire disclosure of which is incorporated herein by reference.

FIELD

The present disclosure relates to multi-armed polyoxazolines, compositions containing the multi-armed polyoxazolines, methods of making multi-armed polyoxazolines, and methods of using multi-armed polyoxazolines, among other aspects. The multi-armed polyoxazolines of the present disclosure are useful, for example, in various biomedical applications.

BACKGROUND

Bioerodible injectable hydrogels are a newly emerging class of materials having a variety of medical uses.

As one specific example, in the case of SpaceOAR®, a long-term bioerodible injectable hydrogel based on multi-arm PEG-based, such products are used to create or maintain space between tissues in order to reduce side effects of off-target radiation therapy. See "Augmenix Announces Positive Three-year SpaceOAR Clinical Trial Results," *Imaging Technology News*, Oct. 27, 2016. As another specific example, Augmenix has developed TraceIT® Hydrogel, a bioerodible injectable hydrogel synthetic hydrogel consisting primarily of water and iodinated cross-linked polyethylene glycol (PEG) that is visible under CT, cone beam, ultrasound and MR imaging and is useful as a tissue marker (e.g., for targeted radiation therapy). See "Augmenix Receives FDA Clearance to Market its TraceIT™ Tissue Marker," *BusinessWire* Jan. 28, 2013. TraceIT® hydrogel remains stable and visible in tissue for three months, long enough for radiotherapy, after which it is absorbed and cleared from the body. Id. *Augmenix Receives FDA Clearance to Market its TraceIT™ Tissue Marker," BusinessWire* Jan. 28, 2013.

There is a continuing need in the biomedical arts for additional hydrogels, including bioerodible injectable hydrogels, for precursors of such hydrogels, for methods of making such hydrogels and precursors, for methods of using such hydrogels and precursors, and for systems for forming such hydrogels, among other needs.

SUMMARY

In some aspects, the present disclosure pertains to multi-arm polymers comprising a core and a plurality of polyoxazoline segments (or arms) having a first end that is covalently attached to the core and a second end comprising a moiety that comprises a reactive end group.

In some embodiments, which can used in conjunction with the above aspects, the polyoxazoline segments comprise one or more polymerized monomers selected from oxazoline and 2-alkyl-2-oxazolines.

In some embodiments, which can used in conjunction with any of the above aspects and embodiments, the core of the multi-arm polymers may be selected from a polyol residue core and a calyx[n]arene core.

In some embodiments, which can used in conjunction with any of the above aspects and embodiments, wherein the reactive end groups are electrophiles. For example, the reactive end groups may be selected from N-hydroxysuccinimide esters, imidazole esters, imidizole carboxylates and benzotriazole esters, among other possibilities.

In some embodiments, which can used in conjunction with any of the above aspects and embodiments, the reactive end groups may be nucleophiles. For example, the reactive end groups may be amine groups or thiol groups, among other possibilities.

In some embodiments, which can used in conjunction with any of the above aspects and embodiments, the moiety that comprises a reactive end group may further comprise a hydrolysable ester group.

In some embodiments, which can used in conjunction with any of the above aspects and embodiments, the moiety that comprises a reactive end group may comprise a diester. For example, the diester may be selected from a malonic-acid-based diester, a succinic-acid-based diester, a glutaric-acid-based diester and an adipic-acid-based diester.

In other aspects, systems are provided that comprise (a) a first composition comprising a multi-arm polymer in accordance with any of the above aspects and embodiments and (b) a second composition comprising a multifunctional compound that comprises functional groups that are reactive with the reactive end groups of the multi-arm polymer.

In some embodiments, which may use in conjunction with these aspects, the reactive groups of the multi-arm polymer may be selected from one of electrophilic groups and nucleophilic groups and the functional groups of the multifunctional compound may be selected from the other of the electrophilic groups and the nucleophilic groups. For instances, in certain embodiments, the reactive groups may be electrophilic groups, for example, N-hydroxysuccinimide ester groups, and the functional groups may be nucleophilic groups, for example, amine groups or thiol groups.

In some embodiments, which can used in conjunction with any of the above aspects and embodiments, the system may further comprise a delivery device. For example, the delivery device may comprises a first reservoir containing the first composition and a second reservoir containing the second composition.

In still other aspects, the present disclosure provides crosslinked reaction products of (a) a multi-arm polymer in accordance with any of the above aspects and embodiments and (b) a multifunctional compound in accordance with any of the above aspects and embodiments.

In addition to the above, further aspects and embodiments of the present disclosure will become readily apparent upon review of the Detailed Description to follow.

DETAILED DESCRIPTION

In various aspects of the present disclosure, multifunctional initiator molecules are provided that comprise a core and a plurality oxazoline polymerization groups attached to said core.

Figure 1:
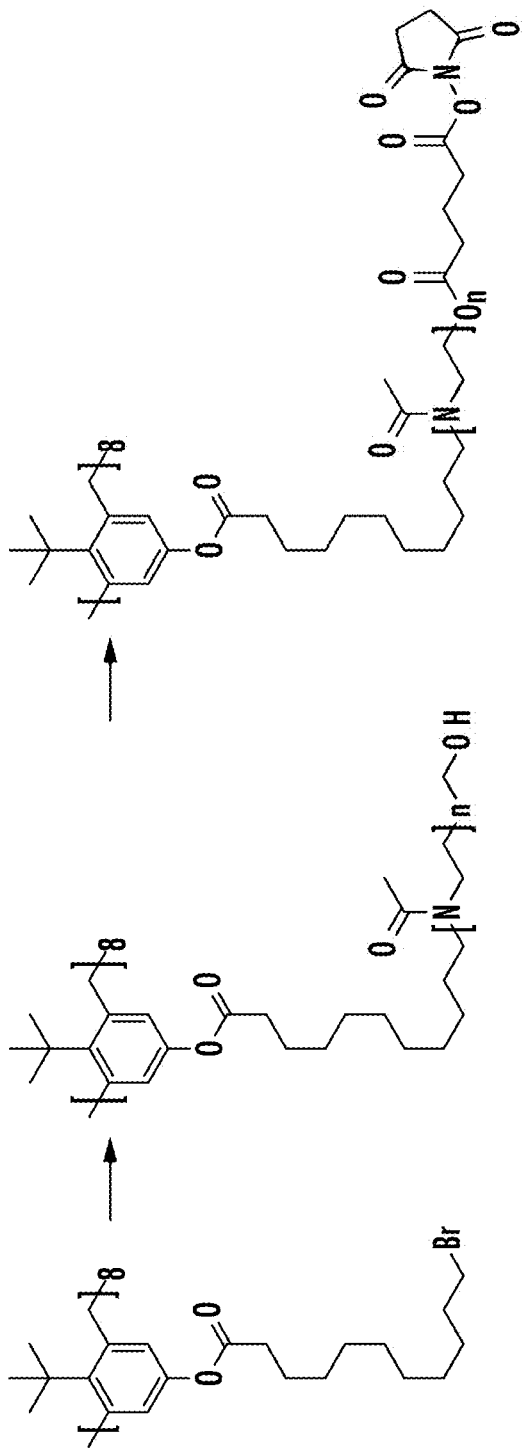
FIG. 1 is a schematic illustration of a method of forming a multi-arm polyoxazoline having a calixarene core and terminal hydroxyl groups, which is subsequently converted into a multi-arm polyoxazoline that is terminated with reactive succinimidyl glutarate groups, in accordance with an embodiment of the present disclosure.

In various embodiments, multifunctional initiator molecules may be provided that comprise a calixarene core, for example a calix[n]arene core, where n ranges from 4-12, among other possibilities, including 4-alkylcalyix[n]arene core such a 4-tert-butylcalix[n]arene core, which is derivatized to have a plurality of oxazoline polymerization groups attached to the core. For example, the oxazoline polymerization groups may comprise a plurality of haloalkyl groups, for instance, a plurality of 1-bromoalkyl groups such as a plurality of omega-bromo-$C_4$-$C_{18}$-alkyl groups, which may be attached to the calix[n]arene core by a suitable linkage, such as an ester or an ether linkage. In a particular example shown in FIG. 1, a multifunctional initiator molecule is provided which comprises a 4-tert-butylcalix[8]arene core substituted with eight omega-bromo-$C_{10}$-alkyl groups.

In various embodiments, multifunctional initiator molecules may be provided by derivatizing a polyol with a plurality of oxazoline polymerization groups, for example, a plurality of sulfonate esters such as a toluene sulfonate ester (e.g., formed by reaction of tosyl chloride with the polyol), an alkanesulfonic acid ester such as a methanesulfonate ester or an alkanesulfonic acid ester derivate such as a trifluoromethanesulfonate ester (e.g., formed by reaction of an alkanesulfonic acid chloride or alkanesulfonic acid chloride derivative with the polyol).

Illustrative polyols for use in forming alkoxyamine molecules include, for example, straight-chained, branched and cyclic aliphatic polyols including straight-chained, branched and cyclic polyhydroxyalkanes, straight-chained, branched and cyclic polyhydroxy ethers and polyhydroxy polyethers, straight-chained, and branched and cyclic polyhydroxyalkyl ethers and polyhydroxyalkyl polyethers, straight-chained, branched and cyclic sugars and sugar alcohols, such as glycerol, mannitol, sorbitol, inositol, xylitol, quebrachitol, threitol, arabitol, erythritol, adonitol, dulcitol, fucose, ribose, arabinose, xylose, lyxose, rhamnose, galactose, glucose, fructose, sorbose, mannose, pyranose, altrose, talose, tagatose, pyranosides, sucrose, lactose, or maltose, oligomers (defined herein as ranging from two to ten units, including dimers, trimers, tetramers, pentamers, hexamers, heptamers, octamers, enneamers or decamers) and polymers (defined herein as eleven or more units) of straight-chained, branched and cyclic sugars and sugar alcohols, including the preceding sugars and sugar alcohols, starches, amylose, dextrins, cyclodextrins, polyhydroxy crown ethers, or polyhydroxyalkyl crown ethers, and aromatic polyols including 1,1,1-tris(4'-hydroxyphenyl) alkanes, such as 1,1,1-tris(4-hydroxyphenyl)ethane, and 2,6-bis(hydroxyalkyl)cresols, among others. In certain preferred embodiments, the polyol is an oligomer of a sugar alcohol such as glycerol, mannitol, sorbitol, inositol, xylitol, or erythritol. In general, a polyol may be selected which contains at least two hydroxyl groups, for example, between 3 and 12 hydroxyl groups in certain embodiments.

Figure 2:
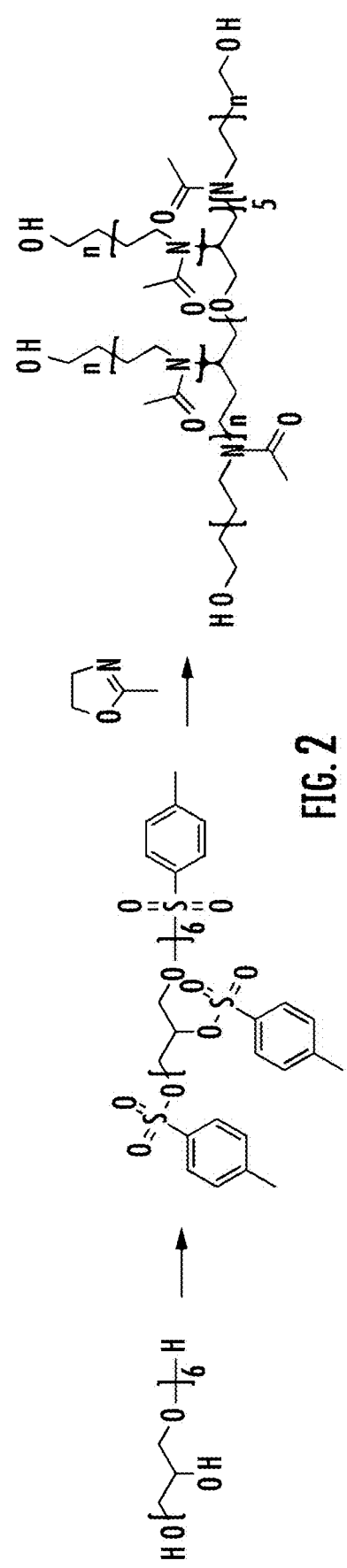
FIG. 2 is a schematic illustration of a method of forming a multi-arm polyoxazoline having a polyol residue core and terminal sulfonate ester groups, which is subsequently converted into a multi-arm polyoxazoline that is terminated with reactive succinimidyl glutarate groups, in accordance with an embodiment of the present disclosure.

With reference to the first step of FIG. 2, a polysulfonate ester, in particular, a polytoluenesulfonate ester with a polyol residue core, specifically a tripentaerythritol residue core may be prepared by reaction of a polyol, specifically, tripentaerythritol, with a sulfonic acid chloride, specifically tosyl chloride to form a multifunctional initiator molecule comprising a core and a plurality oxazoline polymerization groups.

The above and other multifunctional initiator molecules can then be used for the formation of multi-arm (e.g., having 2, 3, 4, 5, 6, 7, 8, 9, 10 or more arms) polyoxazolines, including multi-arm poly(2-oxazolines), for instance, multi-arm poly(2-alkyl-2-oxazolines) via ring opening polymerization of one or more oxazoline monomers selected from oxazoline and 2-oxazolines, including 2-alkyl-2-oxazolines such as 2-methyl-2-oxazoline, 2-ethyl-2-oxazoline, 2-propyl-2-oxazoline, or 2-butyl-2-oxazoline, among others.

Using the above and other techniques, a multi-arm polyoxazolines may be formed, which comprise a core (e.g., a polyol residue core or a calix[n]arene core) and a plurality of polyoxazoline segments, each having a first end and a second end, and each formed from polymerization of at least one type of oxazoline monomer, wherein the first end is linked to the core and the second end comprises a hydroxyl group. For example, as seen from FIG. 1, a haloalkyl substituted calix[8]arene can be used to initiate polymerization of an oxazoline monomer, specifically 2-methyl-2-oxazoline, to form a calix[8]arene core with eight hydroxyl-terminated poly(2-methyl-2-oxazoline) arms. See also Ten'kovtsev, A. V., Trofimov, A. E., Shcherbinskaya, L. I., Thermoresponsive star-shaped poly(2-isopropyl-2-oxazolines) based on octa-tert-butylcalix[8]arene. *Polym Sci Ser B*+2012, 54 (3-4), 142-148. As another example, as seen from FIG. 2, a polysulfonate ester of a polyol, specifically, a toluene sulfonate ester of tripentaerythritol, can be used to initiate polymerization of an oxazoline monomer, specifically 2-methyl-2-oxazoline, to form a calix[8]arene core with eight hydroxyl-terminated poly(2-methyl-2-oxazoline) arms. See also Dworak, A., Trzebicka, B., Kowalczuk, A., Utrata-Wesolek, A., Walach, W., Libera, M., Kronek, J., Thermosensitive star polymers—synthesis and properties. *Polimery-W* 2012, 57 (6), 441-448., Hoogenboom, R., Fijten, M. W., Kickelbick, G., Schubert, U. S., Synthesis and crystal structures of multifunctional tosylates as basis for star-shaped poly(2-ethyl-2-oxazoline)s. *Beilstein J. Org. Chem.* 2010, 6, 773-83.

Figure 3:
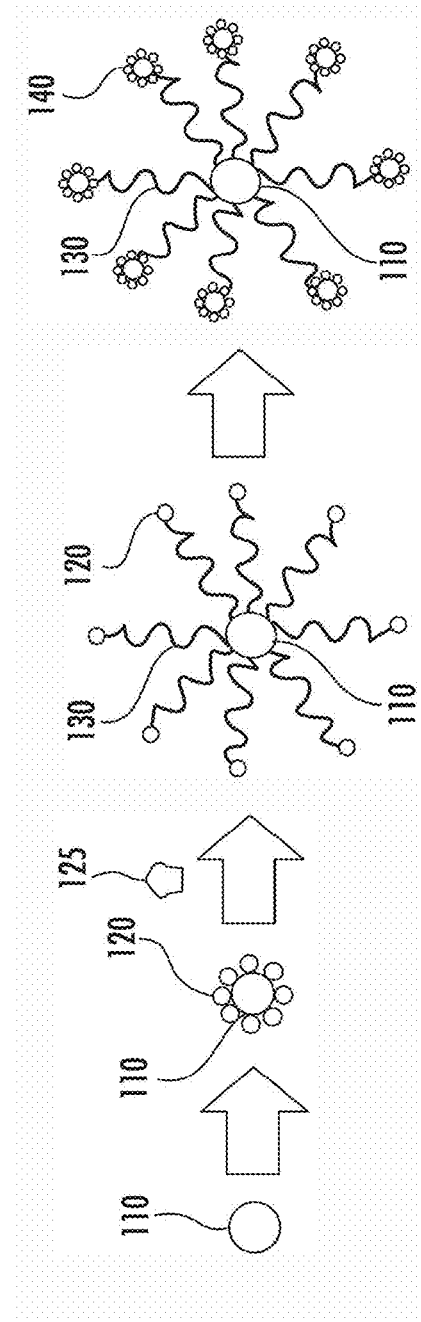
FIG. 3 is a schematic illustration of a method of making a reactive multi-arm polyoxazoline, in accordance with an embodiment of the present disclosure.

The formation the above and other multi-arm polyoxazolines is shown schematically in FIG. 3, in which a polyfunctional molecule 110 (e.g., a polyol, a calix[n]arene, or any other molecule having multiple functional groups that facilitate living cationic polymerization) is used to form a multifunctional initiator molecule having a multiple polymerization groups 120 (e.g., an initiator molecule comprising multiple haloalkyl groups or multiple sulfonate ester groups). Subsequently, polymerization of an oxazoline monomer 125 proceeds from the multifunctional initiator molecule to form a multi-arm polyoxazoline that comprises a core 110 (e.g., a polyol residue, a calix[n]arene core, etc.) and a plurality of polyoxazoline segments 130 extending therefrom, each having a first end and a second end, wherein the first end is linked to the core 110. In the embodiment shown, the second end of each polyoxazoline segment 130 comprises a hydroxyl group 120 (e.g., an alkoxyamine group).

In various embodiments, a reactive multi-arm polyoxazoline may be formed that comprises a core (e.g., a polyol residue or a calix[n]arene core, among others) and a plurality of polyoxazoline segments, each having a first end and a second end, and each formed from at least one type of oxazoline monomer, wherein the first end is linked to the core and the second end comprises a reactive group. For example, as shown schematically in FIG. 3, a moiety comprising a reactive group 140 may be provided at the second end of each polyoxazoline segment 130. In certain embodiments, the moiety further comprises a hydrolysable ester group positioned between the reactive group 140 and the polyoxazoline segment.

The reactive groups of the reactive multi-arm polyoxazoline may be, for example, electrophilic groups or nucleophilic groups. In certain embodiments, the reactive groups of the reactive multi-arm polyoxazoline may be electrophilic groups selected from imidazole esters, imidazole carboxylates, benzotriazole esters, and imide esters, including N-hydroxysuccinimidyl esters, among others. In certain embodiments, the reactive groups of the reactive multi-arm polyoxazoline may be nucleophilic groups selected from amine groups and thiol groups, among others.

In particular embodiments, a reactive multi-arm polyoxazoline may be formed by reacting (a) a polyoxazoline that comprises a core (e.g., a polyol residue or a calix[n]arene core, among others) and a plurality of polyoxazoline segments, each having a first end and a second end, formed from at least one type of oxazoline monomer, wherein the first end is linked to the core and the second end comprises a hydroxyl group with (b) a cyclic anhydride (e.g., glutaric anhydride, succinic anhydride, malonic anhydride, etc.) to form a reaction product (c) in the form of a polyoxazoline that comprises the core and the plurality of polyoxazoline segments, wherein the first end of the polyoxazoline segment is linked to the core and the second end comprises moiety that comprises a carboxylic acid group and a hydrolysable ester group positioned between the carboxylic acid group and the polyoxazoline segment. Subsequently, the reaction product (c) may be treated with a coupling agent (e.g., a carbodiimide coupling agent such as N,N'-dicyclohexylcarbodiimide (DCC), 1-Ethyl-3-(3-dimethylaminopropyl)carbodiimide (EDC), N-Hydroxybenzotriazole (HOBt), BOP reagent, and/or another coupling agent) and N-hydroxysuccinimde (NHS), to yield a multi-arm polyoxazoline comprising succinimidyl end groups, in particular, a polyoxazoline that comprises the core and the plurality of polyoxazoline segments, wherein the first end of the polyoxazoline segments is linked to the core and the second end comprises a moiety that comprises a hydrolysable ester group and a succinimide ester group.

Reactive multi-arm polyoxazolines formed as described above may be water soluble. Moreover, reactive multi-arm polyoxazolines formed as described above may be crosslinked with a suitable crosslinking agent, either in vivo or ex vivo, to form a crosslinked hydrogel.

In certain embodiments, the reactive multi-arm polyoxazoline may be crosslinked with a multifunctional compound having functional groups that are reactive with the reactive groups of the multi-arm polyoxazoline. For example, in some embodiments, the reactive groups of the reactive multi-arm polyoxazoline are nucleophilic groups and the functional groups of the multifunctional compound group are electrophilic groups. In some embodiments, the reactive groups of the reactive multi-arm polyoxazoline are electrophilic groups and the functional groups of the multifunctional compound are nucleophilic groups.

For example, the functional groups of the multifunctional compound may be electrophilic groups selected from imidazole esters, imidazole carboxylates, benzotriazole esters, imide esters, including N-hydroxysuccinimidyl esters. As another example, the functional groups of the multifunctional compound may be nucleophilic groups selected from amine groups and/or thiol groups.

In some embodiments, the reactive groups of the reactive multi-arm polyoxazoline and the functional groups of the multifunctional compound react with one another via an amide coupling reaction.

In various aspects, the present disclosure pertains to a crosslinkable system comprising (a) a first fluid composition comprising a reactive multi-arm polyoxazoline like that described above, which comprises a core (e.g., a polyol residue or a calix[n]arene core, among others) and a plurality of polyoxazoline segments, each having a first end and a second end, and each formed from at least one type of oxazoline monomer, wherein the first end is linked to the core and the second end comprises a reactive group and, optionally, a hydrolysable ester group that is positioned between the reactive group and the polyoxazoline segment and (b) a second fluid composition comprising a multifunctional compound like that described above, which comprises functional groups that are reactive with the reactive end groups. In some embodiments, the reactive groups of the reactive multi-arm polyoxazoline are electrophilic groups and the functional groups of the multifunctional compound are nucleophilic groups. In some embodiments, the reactive groups of the reactive multi-arm polyoxazoline and the functional groups of the multifunctional compound react with one another via an amide coupling reaction.

In addition to the reactive multi-arm polyoxazoline, the first fluid composition may further comprise, for example, therapeutic agents and/or contrast agents, among other possibilities. In addition to the multifunctional compound, the second fluid composition may further comprise, for example, therapeutic agents and/or contrast agents, among other possibilities.

In various embodiments, the system will include one or more delivery devices for delivering the first and second fluid compositions to a subject. For example, the system may include a delivery device that comprises a first reservoir that contains the first fluid composition, a second contains the first second fluid composition. During operation, the first and second fluid compositions are dispensed from the first and second reservoirs, whereupon the first and second fluid compositions interact and crosslink with one another to form a hydrogel.

In particular embodiments, the system may include a delivery device that comprises a double-barrel syringe, which includes first barrel having a first barrel outlet, which first barrel contains the first fluid composition, a second barrel having a second barrel outlet, which second barrel contains the second fluid composition, a first plunger that is movable in first barrel, and a second plunger that is movable in second barrel. In some embodiments, the device may further comprise a mixing section having a first mixing section inlet in fluid communication with the first barrel outlet, a second mixing section inlet in fluid communication with the second barrel outlet, and a mixing section outlet.

In some embodiments, the device may further comprise a cannula or catheter tube that is configured to receive the first and second fluid compositions from the first and second barrels. For example, a cannula or catheter tube may be configured to form a fluid connection with an outlet of a mixing section by attaching the cannula or catheter tube to an outlet of the mixing section, for example, via a suitable fluid connector such as a luer connector.

As another example, the catheter may be a multi-lumen catheter that comprise a first lumen and a second lumen, a proximal end of the first lumen configured to form a fluid connection with the first barrel outlet and a proximal end of the second lumen configured to form a fluid connection with the second barrel outlet. In some embodiments, the multi-lumen catheter may comprise a mixing section having a first mixing section inlet in fluid communication with a distal end of the first lumen, a second mixing section inlet in fluid communication with a distal end of the second lumen, and a mixing section outlet.

During operation, when the first and second plungers are depressed, the first and second fluid compositions are dispensed from the first and second barrels, whereupon the first and second fluid compositions interact and crosslink to form a hydrogel, which is administered onto or into tissue of a subject.

For example, the first and second fluid compositions may pass from the first and second barrels, into the mixing section via first and second mixing section inlets, whereupon the first and second fluid compositions are mixed to form an admixture, which admixture exits the mixing section via the mixing section outlet. In some embodiments, a cannula or catheter tube is attached to the mixing section outlet, allowing the admixture to be administered to a subject after passing through the cannula or catheter tube.

As another example, the first fluid composition may pass from the first barrel outlet into the first lumen of a multi-lumen catheter and the second fluid composition may pass from the second barrel outlet into the second lumen of the multi-lumen catheter. In some embodiments the first and second fluid compositions may pass from the first and second lumen into a mixing section at a distal end of the multi-lumen catheter via first and second mixing section inlets, respectively, whereupon the first and second fluid compositions are mixed in the mixing section to form an admixture, which admixture exits the mixing section via the mixing section outlet.

In additional aspects, the present disclosure pertains to crosslinked products of (a) a reactive multi-arm polyoxazoline like that described above, which comprises a core (e.g., a polyol residue or a calix[n]arene core, among others) and a plurality of polyoxazoline segments, each having a first end and a second end, and each formed from at least one type of oxazoline monomer, wherein the first end is linked to the core and the second end comprising a moiety that comprise a reactive group and, optionally, a hydrolysable group that is positioned between the reactive group and the polyoxazoline segment and (b) a multifunctional compound that comprises functional groups that are reactive with the reactive end groups. Such crosslinked products may be formed in vivo (e.g., using a delivery device like that described above) or such crosslinked products may be formed ex vivo and subsequently administered to a subject.

In various embodiments, the reaction product of the functional groups of the multifunctional compound with the reactive end groups of the reactive multi-arm polymer comprises amide linkages.

In certain beneficial embodiments, the reactive groups of the reactive multi-arm polyoxazolines for use in the first fluid compositions of the above systems, and for use in forming the above crosslinked products, may be selected from imidazolyl esters, benzotriazole esters, imide esters, including N-hydroxysuccinimidyl esters, and imidazolyl carboxylates, among others.

In certain beneficial embodiments, the multifunctional compound for use in the second fluid compositions of the above systems, and for use in forming the above crosslinked products, may be a polyamine. In general, polyamines suitable for use in the present disclosure include, for example, small molecule polyamines (e.g., containing at least two amine groups, for instance, from 3 to 20 amine groups or more in certain embodiments), comb polymers having amine side groups, and branched polymers having amine end groups, including dendritic polymers having amine end groups.

Particular examples of multifunctional amines which may be used as the multifunctional compound include trilysine, ethylenetriamine, diethylene triamine, hexamethylenetriamine, di(heptamethylene) triamine, di(trimethylene) triamine, bis(hexamethylene) triamine, triethylene tetramine, tripropylene tetramine, tetraethylene pentamine, hexamethylene heptamine, pentaethylene hexamine, dimethyl octylamine, dimethyl decylamine, and JEFFAMINE polyetheramines available from Huntsman Corporation, among others. Further particular examples of multifunctional amines include polypeptides including poly(L-lysine), chitosan, and poly(allyl amine), among others.

Figure 4:
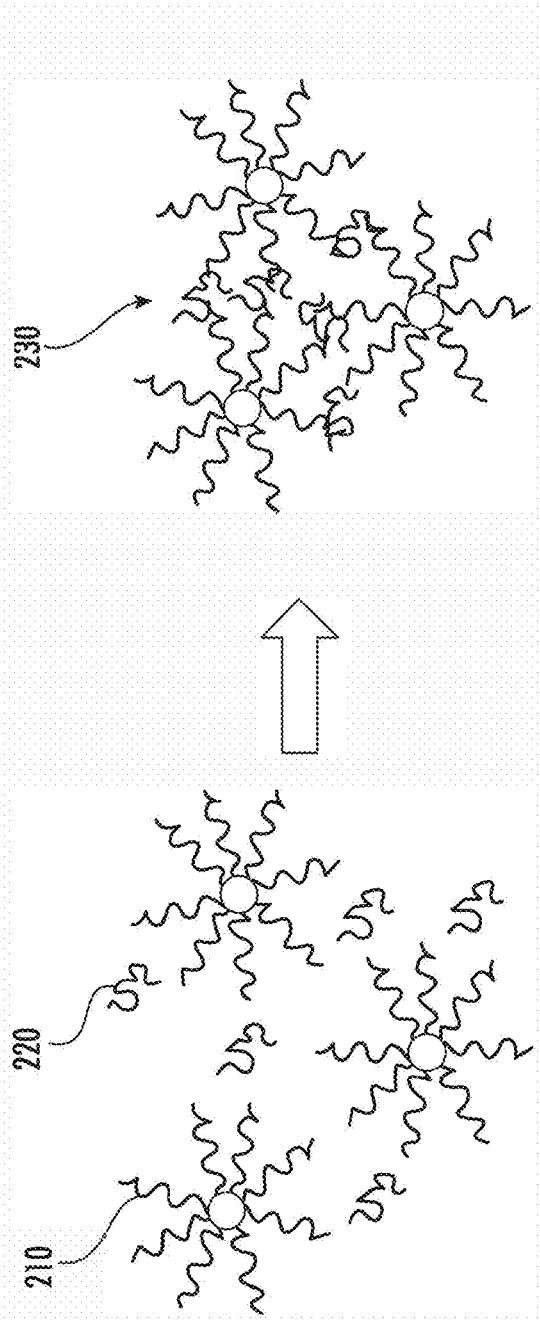
FIG. 4 is a schematic illustration of a method of crosslinking a reactive multi-arm polyoxazoline with a multifunctional crosslinking agent, in accordance with an embodiment of the present disclosure.

As shown schematically in FIG. 4, a reactive multi-arm polyoxazoline 210 like that described above (e.g., comprising a core, such as a polyol residue or a calix[n]arene core, and a plurality of polyoxazoline segments, each polyoxazoline segment terminated with a succinimidyl-group) is crosslinked with a multifunctional compound 220 comprising functional groups that are reactive with the reactive groups of the multi-arm polyoxazoline 210 (e.g., a polyamine such as trilysine) to form a crosslinked product 230.

Compositions comprising the multi-arm polyoxazolines as described herein, as well as compositions comprising the cross-linked polyoxazolines described herein (i.e., cross-linked products of the multi-arm polyoxazolines described herein with the multifunctional compounds as described herein), can be used in a wide variety of biomedical applications, including medical devices, implants, and pharmaceutical compositions.

In various embodiments, compositions can be formed that include the multi-arm polyoxazolines described herein as well as one or more additional agents. In various embodiments, compositions can be formed that include the cross-linked polyoxazolines described herein as well as one or more additional agents.

Examples of such additional agents include therapeutic agents and imaging agents, among others.

Examples of imaging agents include (a) fluorescent dyes such as fluorescein, indocyanine green, or fluorescent proteins (e.g. green, blue, cyan fluorescent proteins), (b) contrast agents for use in conjunction with magnetic resonance imaging (MRI), including contrast agents that contain elements that form paramagnetic ions, such as $Gd^{(III)}$, $Mn^{(II)}$, $Fe^{(III)}$ and compounds (including chelates) containing the same, such as gadolinium ion chelated with diethylenetriaminepentaacetic acid, (c) contrast agents for use in conjunction with ultrasound imaging, including organic and inorganic echogenic particles (i.e., particles that result in an increase in the reflected ultrasonic energy) or organic and inorganic echolucent particles (i.e., particles that result in a decrease in the reflected ultrasonic energy), (d) contrast agents for use in connection with x-ray fluoroscopy, including metals and metal compounds (e.g., metal salts, metal oxides, etc.), for instance, barium compounds, bismuth compounds and tungsten, among others, and iodinated compounds, among others, (e) radiocontrast agents, such as those based on the clinically important isotope $^{99m}$Tc, as well as other gamma emitters such as $^{123}$I, $^{125}$I, $^{131}$I, $^{111}$In, $^{57}$Co, $^{153}$Sm, $^{133}$Xe, $^{51}$Cr, $^{81m}$Kr, $^{201}$Tl, $^{67}$Ga and $^{75}$Se, among others, (f) positron emitters, such as $^{18}$F, $^{11}$C, 13N, $^{15}$O, and $^{68}$Ga, among others, may be employed to yield functionalized radiotracer coatings, and (g) contrast agents for use in connection with near-infrared (NIR) imaging, which can be selected to impart near-infrared fluorescence to the coatings of the present disclosure, allowing for deep tissue imaging and device marking, for instance, NIR-sensitive nanoparticles such as gold nanoshells, carbon nanotubes (e.g., nanotubes derivatized with hydroxyl or carboxyl groups, for instance, partially oxidized carbon nanotubes), dye-containing nanoparticles, such as dye-doped nanofibers and dye-encapsulating nanoparticles, and semiconductor quantum dots, among others. NIR-sensitive dyes include cyanine dyes, squaraines, phthalocyanines, porphyrin derivatives and borondipyrromethane (BODIPY) analogs, among others.

Compositions in accordance with the present disclosure include lubricious compositions for medical applications, compositions for therapeutic agent release (e.g., by including one or more therapeutic agents in a matrix of the crosslinked polyoxazolines, by using the crosslinked polyoxazolines to encapsulate one or more therapeutic agents, etc.), implants, which may be formed ex vivo or in vivo (e.g., composition for use as tissue markers, compositions that act as spacers to reduce side effects of off-target radiation therapy, etc.).

The invention claimed is:

1. A system comprising (a) a first composition comprising a multi-arm polymer comprising a polyol residue core and three or more polyoxazoline segments having a first end that is covalently attached to the polyol residue core and a second end comprising a moiety that comprises an electrophilic reactive group and (b) a second composition comprising a multifunctional polyamine compound that comprises three or more amine functional groups that are reactive with the reactive groups of the multi-arm polymer.

2. The system of claim 1, wherein the first composition, the second composition, or both, further comprise a therapeutic agent.

3. The system of claim 1, further comprising a delivery device.

4. The system of claim 3, wherein the delivery device comprises a first reservoir containing the first composition and a second reservoir containing the second composition.

5. The system of claim 1, wherein the multi-arm polymer comprises between 4 and 12 of the polyoxazoline segments.

6. The system of claim 1, wherein the polyoxazoline segments comprise one or more polymerized monomers selected from oxazoline and 2-alkyl-2-oxazolines.

7. The system of claim 1, wherein the reactive group is selected from N-hydroxysuccinimide esters, imidazole esters, imidizole carboxylates and benzotriazole esters.

8. The system of claim 1, wherein the moiety that comprises the reactive group further comprises a hydrolysable ester group.

9. The system of claim 1, wherein the moiety that comprises the reactive group comprises a diester.

10. The system of claim 9, wherein the diester is selected from a malonic-acid-based diester, a succinic-acid-based diester, a glutaric-acid-based diester and an adipic-acid-based diester.

11. The system of claim 1, wherein the multi-arm polymer comprises between 6 and 10 of the polyoxazoline segments.

12. The system of claim 1, wherein the polyol residue is a residue of a polyol selected from straight-chained, branched and cyclic aliphatic polyols, straight-chained, branched and cyclic polyhydroxy ethers, straight-chained, branched and cyclic polyhydroxy polyethers.

13. The system of claim 1, wherein the polyol residue is a residue of a polyol having between 3 and 12 hydroxyl groups.

14. The system of claim 1, wherein the polyol residue is selected from residues of straight-chained, branched and cyclic sugars and sugar alcohols, and oligomers of straight-chained, branched and cyclic sugars and sugar alcohols.

15. A crosslinked reaction product of (a) a first composition comprising a multi-arm polymer comprising a polyol residue core and three or more polyoxazoline segments having a first end that is covalently attached to the polyol residue core and a second end comprising a moiety that comprises an electrophilic reactive group and (b) a second composition comprising a multifunctional polyamine compound that comprises three or more amine functional groups that are reactive with the reactive groups of the multi-arm polymer.

16. The crosslinked reaction product of claim 15, wherein the first composition, the second composition, or both, further comprise a therapeutic agent.

17. A method comprising delivering to a subject a mixture comprising: a multi-arm polymer comprising a polyol residue core and three or more polyoxazoline segments having a first end that is covalently attached to the polyol residue core and a second end comprising a moiety that comprises an electrophilic reactive group and a multifunctional polyamine compound that comprises three or more amine functional groups that are reactive with the reactive groups of the multi-arm polymer to subject, wherein crosslinked hydrogel is formed in vivo in the subject.

18. The method of claim 17, wherein the mixture further comprises a therapeutic agent.

\* \* \* \* \*